United States Patent [19]

Petty

[11] 4,350,642
[45] Sep. 21, 1982

[54] PROCESS FOR PREPARATION OF A PESTICIDAL PHENYLACETATE ENANTIOMER PAIR

[75] Inventor: Walter L. Petty, Houston, Tex.
[73] Assignee: Shell Oil Company, Houston, Tex.
[21] Appl. No.: 244,372
[22] Filed: Mar. 16, 1981
[51] Int. Cl.³ .................. C07C 121/66; C07C 121/75
[52] U.S. Cl. ............................... 260/465 D; 424/304
[58] Field of Search .................................. 260/465 D

[56] References Cited

U.S. PATENT DOCUMENTS 4,176,195 11/1979 Stoutamire .......................... 424/304
4,238,406 12/1980 Suzuki et al. .................... 260/465 D

FOREIGN PATENT DOCUMENTS 2013206 8/1979 United Kingdom ........... 260/465 D

Primary Examiner—Dolph H. Torrence

[57] ABSTRACT

A pesticidal phenylacetate Y enantiomer pair is prepared by precipitating crystals of novel phenylacetate X enantiomer pair in the presence of crystals of phenylacetate X from a solution of racemic phenylacetate and recovering the filtrate rich in the Y enantiomer pair. The phenylacetate X crystals can be redissolved, epimerized and the epimerizaion product recycled to improve the yield of phenylacetate Y enantiomer pair.

23 Claims, No Drawings

PROCESS FOR PREPARATION OF A PESTICIDAL PHENYLACETATE ENANTIOMER PAIR

BACKGROUND OF THE INVENTION

1. Field of the Invention

This invention relates to a process for the preparation of a pesticidal phenylacetate Y-rich enantiomer pair and to a novel crystalline X enantiomer pair.

2. Description of the Prior Art

U.S. Pat. No. 4,176,195 discloses an enantiomer pair consisting of S-α-cyano-3-phenoxybenzyl S-α-isopropyl-p-chlorophenylacetate and R-α-cyano-3-phenoxybenzyl R-α-isopropyl-p-chlorophenylacetate as a highly active pesticide and its preparation by crystallization or chromatography. U.S. Pat. No. 4,238,406 discloses a process for preparing this enantiomer pair or a mixture rich in this pair by precipitating crystals of the pair from the corresponding racemic mixture by seeding with crystals of the pair or of an isomer of the pair optionally in the presence of a basic catalyst. This enantiomer pair is referred to as the Y form.

SUMMARY OF THE INVENTION

The present invention provides a process for preparing an enantiomer pair consisting of S-α-cyano-3-phenoxybenzyl S-α-isopropylphenylacetates and the corresponding R-α-cyano-3-phenoxybenzyl R-α-isopropylphenylacetates, hereinafter referred to as phenylacetate Y. The present invention also provides a novel intermediate whose properties are important to the operability of the process. This previously unknown intermediate is the crystalline enantiomer pair consisting of S-α-cyano-3-phenoxybenzyl R-α-isopropylphenylacetates and the corresponding R-α-cyano-3-phenoxybenzyl S-α-isopropylphenylacetates, hereinafter referred to as phenylacetate X and crystals enriched in phenylacetate X.

The crystalline enantiomer pair phenylacetate X of the invention can be prepared from the corresponding racemic R,S-α-cyanobenzyl alcohol R,S-α-isopropylphenylacetate by passing the racemate through a chromatographic column containing a suitable packing material, for example, silica gel, using an eluant liquid, for example, 1% diethyl ether in hexane. The phenylacetate X enantiomer pair is recovered as the earlier emerging of the two enantiomer pairs. Crystalline phenylacetate X can then be obtained by cooling the resulting phenylacetate X from the chromatographic separation. The cooling (crystallization) is conducted at any temperature at which phenylacetate X crystals form, for example, at about −50° to about 20° C. and, preferably about −15° to about 5° C. The crystalline enantiomer pair phenylacetate X is usually recovered in about 64% purity, further recrystallizations yield a product phenylacetate X of purity of at least 75% and usually above at least 80% or even above 95%. Crystals enriched in the phenylacetate X enantiomers (phenylacetate X crystals and other crystalline forms of either of the X diastereoisomers) are also formed during in situ cooling the above described racemate in a solvent, for example, methanol, from which the desired phenylacetate X-enriched crystals spontaneously preferentially crystallizes without the addition of phenylacetate X seed crystals, for example, as in the process of the invention described below and Example I. Repeated recrystallization of the crude crystals, as in Example II below, yields phenylacetate X of high purity and melting point of 68° C. Crystals of phenylacetate Y have a melting point range and appear to be mixtures of crystals of each of the two isomers which comprise phenylacetate Y. The phenylacetate X crystals have markedly different and unique properties from those of crystalline phenylacetate Y. These unique and different properties include a higher and sharper melting point than crystalline phenylacetate Y, which indicates that phenylacetate X is a crystalline racemic compound of the two enantiomers which comprise phenylacetate X rather than a mixture of crystals of each of the two enantiomers as in crystalline phenylacetate Y. In addition, it has been discovered that the solubility of crystalline phenylacetate Y is from about 2 to about 4 times greater than that of crystalline phenylacetate X or of phenylacetate X-enriched crystals and that phenylacetate X has a very much faster rate of crystallization than phenylacetate Y. The above described properties of crystalline phenylacetate X and phenylacetate X-enriched crystals are useful in the process of the invention described below.

The process of the present invention comprises precipitating crystals of phenylacetate X (and other crystalline forms enriched in either of the X diastereoisomers) in the presence of crystals of phenylacetate X from a solution of the corresponding racemic R,S-α-cyano-3-phenoxybenzyl R,S-α-isopropylphenylacetate, separating these phenylacetate X-enriched crystals from the mother liquor, redissolving them in a solvent and treating the resulting solution with a base to epimerize the phenylacetate X to the corresponding racemic mixture, recycling the racemic mixture back to the precipitation step and recovering mother liquor enriched in phenylacetate Y.

U.S. Pat. No. 4,238,406 describes a process of preparing phenylacetate Y by crystallization from the corresponding racemate in the presence of seed crystals of phenylacetate Y. Phenylacetate X-enriched mother liquors are not crystallized but instead are epimerized to form an essentially racemic recycle stream. Thus, the process of the invention is quite different from that described in the above U.S. patent. Once the initial phenylacetate X or X-enriched crystals are formed, it is very difficult to obtain crystals of phenylacetate Y. The present process overcomes this problem of obtaining crystals of phenylacetate Y and takes advantage of the previously unknown and different properties of crystalline phenylacetate X and phenylacetate X-enriched crystals. It is now possible and desirable to obtain phenylacetate Y in liquid rather than solid form and without the use of seed crystals of phenylacetate Y. Also, the very much faster crystallization of phenylacetate X or X-enriched crystals allows the use of a multi-stage, continuous crystallizer, if desired, in place of very large batch crystallizers. Continuous processing is often preferred over the batch processing for both technical and economic reasons.

Phenylacetates which can be used to prepare their corresponding phenylacetate Y product and novel crystalline phenylacetate X and novel crystalline phenylacetate X-enriched intermediate have the formula I

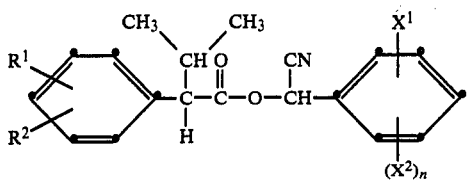

wherein $R^1$ is a hydrogen atom, a halogen atom having an atomic number of from 9 to 53, inclusive, or an alkyl group containing from 1 to 4 carbon atoms or an alkoxy group containing from 1 to 2 carbon atoms, each optionally substituted by one or more halogen atoms having an atomic number of from 9 to 53, inclusive, $R^2$ is a hydrogen atom or a methyl group, $X^1$ is phenoxy, benzyl or phenylthio, $X^2$ is a halogen atom having an atomic number of from 9 to 35, inclusive, or is methyl and n is 0, 1 or 2.

Preferably, $R^1$ is a halogen atom or an optionally halogenated alkyl or alkoxy group as defined above, for example, $R^1$ is a chlorine or fluorine atom, methyl, ethyl, isopropyl, tert-butyl, methoxy, ethoxy, difluoromethoxy or trifluoromethoxy and $R^2$ is a hydrogen atom. $R^1$ is preferably located at the meta- or para-position relative to the benzyl carbon atom in the acid moiety. Preferably, $R^1$ is located at the paraposition.

Preferred because of their pesticidal properties are those pyrethroid esters of formula I wherein n is 0 and $X^1$ is located in the 3-position relative to the benzyl carbon atom in the alcohol moiety. Especially useful are those pyrethroid esters of formula I wherein $X^1$ is phenoxy.

Because of their pesticidal properties, it is preferred to prepare a phenylacetate Y product of a material of formula I in which $R^1$ is chlorine or difluoromethoxy, $R^2$ is a hydrogen atom, $X^1$ is 3-phenoxy and n is 0.

Solvents used in the process can be any inert material in which the phenylacetate is at least partly soluble at room temperature.

Examples of suitable classes of solvents include chlorinated hydrocarbons, ethers, nitriles, esters, amides, hydroxylic solvents and the like. Suitable hydroxylic solvents include lower alkanols containing from 1 to 4 carbon atoms such as isopropanol, butanol, ethanol, and methanol, and preferably containing from 1 to 2 carbon atoms, especially methanol. Other suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between about 40° to about 65° C., between about 60° to about 80° C. or between about 80° to about 110° C. Petroleum ether is also suitable. Cyclohexane and methycyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene. Ethers are generally those containing from 4 to 6 carbon atoms such as diethyl ether, methyl tert-butyl ether and diisopropyl ether. Tetrahydrofuran and dioxane are also useful. Nitriles usually also contain from 2 to 6 carbon atoms, for example, acetonitrile and the like. Esters are those of lower alcohols and acids each containing from 2 to 6 carbon atoms, for example, ethyl acetate. Amides are those of lower alkyl amines and acids each containing from 1 to 6 carbon atoms, for example, dimethylformamide.

While different solvents may be employed in the crystallization and epimerization steps, it is desirable to use the same solvent in both steps, with alkanes and alkanols being preferred. Alkanols containing 1 to 4 carbon atoms are particularly useful, especially methanol.

The epimerization catalyst is any basic agent, e.g., inorganic or organic in nature, which does not itself form stable reaction products with the cyanohydrin ester and preferably has a $pK_b$ of less than 6. Examples of suitable inorganic compounds include hydroxides, carbonates, hydrides, and cyanides of alkali and alkaline earth metals, and metal oxides such as sodium cyanide, sodium hydroxide, barium hydroxide, potassium hydroxide, calcium carbonate, sodium carbonate, calcium oxide, alumina, zinc oxide and the like.

Suitable organic bases are alkali or alkaline earth metal salts of weak organic acids or organic nitrogen bases, alkali metal alcoholates and alkali metal amides. Suitable salts include sodium acetate, magnesium formate, potassium tert-butylate, sodium isopropylate and the like. Nitrogen bases can be ammonia, ammonium hydroxide or any alkyl, aryl or heterocyclic nitrogen base including mono- or polyamines and the like. Preferably, the organic nitrogen base is an amine in which any alkyl groups contain from 1 to 10 carbon atoms, any aryl or aralkyl groups contain from 6 to 20 carbon atoms and 1 to 2 hydrocarbyl rings, and any heterocyclic amines contain at least one ring nitrogen atom in a 5 or 6 membered heterocyclic ring optionally containing a sulfur or oxygen atom or another nitrogen atom, such as trimethylamine, diethylamine, triethylamine, piperidine, isoamylamine, benzylamine, 1-naphthylamine, diethylamine, tri-n-propylamine, ephedrine, tert-butylamine, ethanolamine, triethylenediamine, tetramethylenediamine, pyrrolidine, quinoline, pyridine, morpholine or tetrabutylammonium hydroxide. The amines are preferably secondary and especially tertiary amines containing any combination of the above-described group. When the amine is a tertiary amine it desirably contains three alkyl groups of 1 to 4 carbon atoms, for example: trimethylamine, tri-n-propylamine, and especially triethylamine.

Other suitable basic agents are ion exchange resins having a strong basic character. Such resins include quaternary ammonium and amine ion exchange resins. Resins of this type are often sold under the trade names Dowex and Amberlite, for example, those derived from trimethylamine (such as the products known under the trade names of "Amberlite IRA-400", "Amberlite IRA-40L", "Amberlite IRA-402", "Amberlite IRA-900", "Duolite A-101-D", "Duolite ES-111", "Dowex 1", "Dowex 11", "Dowex 21K" and "Ionac A-450" (all ten trade names are registered trademarks) and those derived from dimethylethanolamine (such as the products known under the trade names of "Amberlite IRA-410", "Amberlite IRA-911", "Dowex 2", "Duolite A-102-D", "Ionac A-542" and "Ionax A-550" (all six trade names are registered trademarks). Very good results have been obtained with those derived from trimethylamine. When these catalysts are available in a neutralized form, for instance in the chloride form, they must be activated to the hydroxyl form by treatment with an aqueous alkali metal hydroxide, for example sodium hydroxide, and washed with water to remove salt anions before use. Also useful as basic agents are high molecular weight liquid amines which are insoluble in water such as the "liquid Amberlites" which are sold commercially as liquid Amberlites of the type LA1 and LA2.

Phosphorus-containing bases are also suitable, such as lower alkyl phosphines like triphenyl phosphine and tri-n-butyl phosphine.

Preferably, the basic agent is ammonia or a tertiary alkyl amine wherein basic agents are triethylamine, and especially ammonia.

The concentration of the epimerization catalyst may vary from about 0.001 to about 100 mole % and suitably from about 0.01 to about 50 mole % based on the amount of racemate, preferably from about 0.05 to about 20 mole % and, especially from about 0.1 to about 15 mole %. Normally about 1 mole % is used.

If desired, a stabilizing amount of an acid is added to the racemic mixture solution prior to crystallization in order to neutralize catalyst or other basic materials and prevent epimerization of the phenylacetate Y in the mother liquor during subsequent crystallization of phenylacetate X-enriched crystals.

While the precise amount of acid needed will depend upon the amount of basic catalyst used or other basic material present, from about 0.001 to about 5% by weight of acid based upon the phenylacetate feed is used. Preferably, from about 0.01 to about 0.5% by weight of acid is used.

Any inorganic or organic acid or acidic acting material which will not undesirably affect the desired product can be used to stabilize the solution, for example, mineral acids, such as hydrochloric or sulfuric acid, sulfonic acids, such as toluenesulfonic acid, or organic acids, including lower alkanoic acids, such as acetic, propionic or butyric acid. Acetic acid is preferred.

Precipitation, e.g. crystallization, is conducted by forming a mixture of the racemate in a suitable solvent as defined above. The process can be conducted at any temperature at which crystals enriched in phenylacetate X enantiomer pair form, suitably from about −50° to about 60° C., preferably from about −35° to about 5° C. and especially from about −15° to about 5° C.

It is often desirable to add substantial amounts of seed crystals to enhance the rate of crystallization. It is usually most convenient to use crystals of the essentially pure phenylacetate X or crystals enriched therein as seed crystals although crystals of either single diastereoisomer in phenylacetate X or a mixture of crystals of both diastereoisomers in phenylacetate X can be used. Use of high purity phenylacetate X seed crystals appear to lead to higher yields of phenylacetate Y in the filtrate. Other known nucleating agents can be used when seed crystals are desired, for example, powdered silica, potassium acetate and the like. The amount of seed crystals used is not critical, but the crystallization is faster than a large amount of seed crystals. The amount of seed may vary from about 0.05 to about 10% based upon the phenylacetate in solution and is preferably about 1%. Of course, as the process progresses, the phenylacetate X crystals being formed also serve as further amounts of seed crystals. The crystals enriched in phenylacetate X produced during the process can be separated and recovered from the crystallization by such methods as filtration, centrifugation or decantation of the mother liquor and the like. The choice of the separation method will in part depend on whether the crystals are to be epimerized in the same vessel in which they were formed or transferred to another vessel as appropriate in a batch, continuous or semi-continuous process.

The epimerization is conducted by forming a solution of phenylacetate X in a suitable solvent as defined above and adding the desired amount of epimerization catalyst to the solution. The process is conducted at any temperature at which epimerization proceeds without significant decomposition of the phenylacetate. The epimerization is much faster at higher temperatures. Suitably, epimerization is conducted at temperatures in the range of from about −50° C. to the reflux temperature of the solvent, preferably from about −20° C. to about 150° C., and especially from about 0° C. to about 50° C.

The product of the epimerization is essentially a solution of racemic phenylacetate. This product can then be combined with fresh quantities of racemic phenylacetate solution, and this resulting mixture again subjected to precipitation (crystallization) under the conditions previously described above.

Neutralization or removal of the residual epimerization catalyst is carried out by known methods. In some cases, catalysts which are insoluble in the solvents of the process are advantageous, for example, basic ion exchange resin catalyst, while in other cases one may add a small amount of acidic material, for example, acetic acid, when utilizing a basic catalyst such as ammonia.

As mentioned earlier, the product phenylacetate Y mother liquor is separated from the phenylacetate X or X-enriched crystals by known methods, for example, by centrifuging off the phenylacetate X or X-enriched crystals. The phenylacetate Y can then be concentrated or separated from the solvent, for example, by flashing off a lighter solvent such as methanol. Other light end impurities can be removed, for example, in a wiped film evaporator.

It will be appreciated by those of skill in the art that the present process can be conducted as a batch, semi-continuous or continuous process employing one or more treatment vessels as appropriate.

PREFERRED EMBODIMENT OF THE INVENTION

The present invention provides a process for preparing the enantiomer pair consisting of a S-α-cyano-3-phenoxybenzyl S-α-isopropyl-p-chlorophenylacetate and the corresponding R-α-cyano-3-phenoxybenzyl R-α-isopropyl-p-chlorophenylacetate (hereinafter referred to as fenvalerate Y) which process comprises precipitating crystals of an enantiomer pair consisting of S-α-cyano-3-phenoxybenzyl R-α-isopropyl-p-chlorophenylacetate and R-α-cyano-3-phenoxybenzyl S-α-isopropyl-p-chlorophenylacetate (hereinafter referred to as fenvalerate X) in the presence of crystals of fenvalerate X from a solution of R,S-α-cyano-3-phenoxybenzyl R,S-α-isopropyl-p-chlorophenylacetate, separating the fenvalerate X crystals from the mother liquor, redissolving the fenvalerate X crystals in a solvent, treating the solution of fenvalerate X with a base to epimerize fenvalerate X to the corresponding racemic fenvalerate, recycling the racemic mixture back to the precipitation step and recovering fenvalerate Y from the mother liquor.

While the various catalysts, reaction conditions and solvents previously described above can be employed to prepare fenvalerate Y, it is preferable to employ as the solvent an alkanol containing from 1 to 4 carbon atoms and as the catalyst ammonia or a tertiary alkylamine containing 1 to 4 carbon atoms in each alkyl group. The use of methanol with triethylamine or especially with ammonia is preferred.

Fenvalerate X crystals have a melting point of 68° C., some 20° higher than crystals which had previously been obtained for fenvalerate Y.

ILLUSTRATIVE EMBODIMENTS

The invention is also described by the following embodiments which are for the purpose of illustration only and should not be regarded as limiting the invention in any way. The identity of the products, including intermediates, was confirmed by gas chromatography (GC) and nuclear magnetic resonance (NMR) spectral analyses as necessary.

EMBODIMENT I

A solution containing 240 g of essentially racemic technical fenvalerate, 4.49 g of potassium acetate (an optional nucleating agent), 0.6 g of water and 520 g of methanol was cooled to below 0° C. Crystals began to grow rapidly, and soon there was a thick cake of crystals at the bottom of the container with supernatant solution above the cake. This mixture was allowed to stand at room temperature for several hours. Then the mixture was shaken to break up chunks of solid and a small portion was filtered. The recovered white solid, after two rinses with ice-cold methanol, was analyzed by GC as 74.2% fenvalerate X. A portion of this solid was recrystallized once from methanol to give 81.3% fenvalerate X.

The filtrate from the first filtration was chilled to 0° C. and more crystals were isolated. These crystals were recrystallized from methanol acidified with acetic acid seven times, each time analyzing the product by GC. The normalized analysis of the final product was 3.7 g of fenvalerate X of 99.8% purity and melting point of 68° C.

EMBODIMENT II

A solution containing 400 g of technical racemic fenvalerate (fenvalerate Y to fenvalerate X ratio of 47.1 to 52.9), 405 g of methanol and 0.2 g of acetic acid were combined and warmed to form a dissolved and homogenized mixture. The mixture was cooled and stirred at 23° C., and 5.0 g of finely-powdered fenvalerate X crystals was added. The temperature of the slurry was slowly lowered to 0° C. during about 5 hours, and a 45.9 g sample of the slurry was withdrawn and stored in the refrigerator for seeding later in the experiment. The remainder of the slurry was allowed to settle, and 360.7 g of the mother liquor was drawn off via a glass filter-stick. The bed of residual crystals was rinsed twice with portions of cold methanol (total 124.1 g) and also drawn off through the filter-stick. A total of 152.6 g was recovered. A GC analysis of the filtrate showed that the fenvalerate Y to fenvalerate X ratio had been increased to 77% to 23%, respectively.

The 359.6 g filtrate from the above crystallization was charged to a 500 ml flask and batch distilled through a 1-inch, 10-tray Oldershaw column to a kettle temperature of 105° C. to recover methanol for recycle. A total of 237 g of distillate was recovered and the crude fenvalerate Y-rich product remaining weighed 106 g. GC analysis indicated that the fenvalerate Y to fenvalerate X ratio in the bottoms product was 79% to 21%, respectively.

To 368 g of the wet crystals remaining after removal of the filtrate and washings from the previous crystallization was added 140 g of methanol recovered from the distillation. The mixture was warmed to 50° C. to dissolve the solids and was held at that temperature, and 0.375 ml of concentrated aqueous ammonia was added in three portions over 137 minutes to catalyze the epimerization. After a total of 250 minutes the reaction mixture was quenched by the addition of 0.265 ml of acetic acid. The fenvalerate Y to fenvalerate X ratio of the mixture was increased from an initial 36% to 64% to a ratio of better than 44% to 56% (based on sample taken after 205 minutes).

The 494 g reaction mixture from the above epimerization was cooled to room temperature, and 106 g of make-up racemic fenvalerate was added, along with the 151 g of methanolic crystal washes from the earlier crystallization and 149 g of make-up methanol from the distillation. This 765 g mixture was homogenized and placed in a bath at 25° C. The 45.2 g of retained seed slurry from the previous crystallization was added, and this mixture was stirred and cooled to 0° C. during 3 hours. The mixture was held at that temperature for an additional 15 hours, whereupon it was worked up in the manner described earlier. A total of 337 g of filtrate was recovered, which GC analysis showed had a fenvalerate Y to fenvalerate X ratio of 85% to 15%, respectively.

This filtrate was distilled, as before, to give 83.6 g of bottoms, which GC analysis showed had a fenvalerate Y to fenvalerate X ratio of 77% to 23%, respectively.

EMBODIMENTS III—X

Following procedures similar to Embodiment I, the crystalline X and the Y forms of α-cyano-3-phenoxybenzyl α-isopropyl-p-(difluoromethoxy)phenylacetate (III and IV), α-cyano-3-phenoxybenzyl α-isopropyl-p-methylphenylacetate (V and VI), α-cyano-3-phenoxybenzyl α-isopropyl-p-fluorophenylacetate (VII and VIII) and α-cyano-3-phenoxybenzyl α-isopropyl-p(tert-butyl)phenylacetate (IX and X) are prepared.

I claim:

1. A method for the preparation of an enantiomer pair phenylacetate Y consisting of an S-α-cyano-3-phenoxybenzyl S-α-isopropylphenylacetate and the corresponding R-α-cyano-3-phenoxybenzyl R-α-isopropylphenylacetate, which process comprises precipitating crystals enriched in phenylacetate X in the presence of crystals of phenylacetate X, consisting of S-α-cyano-3-phenoxybenzyl R-α-isopropylphenylacetate and the corresponding R-α-cyano-3-phenoxybenzyl S-α-isopropylphenylacetate, from a solution of the corresponding racemic R,S-α-cyano-3-phenoxybenzyl R,S-α-isopropylphenylacetate, separating the phenylacetic X-enriched crystals from the mother liquor, redissolving the crystals in a solvent and treating the resulting solution with a base to epimerize the dissolved enantiomer pair phenylacetate X to the corresponding racemic mixture, recycling the racemic mixture back to the precipitation step and recovering mother liquor enriched in phenylacetate Y.

2. A method according to claim 1 wherein the phenylacetate has the formula I

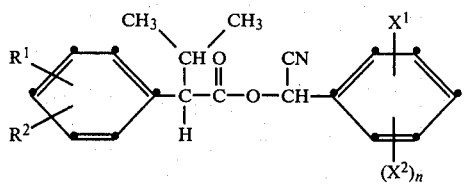

wherein $R^1$ is a hydrogen atom, a halogen atom having an atomic number of from 9 to 53, inclusive, or an alkyl group containing from 1 to 4 carbon atoms or an alkoxy group containing from 1 to 2 carbon atoms, each optionally substituted by one or more halogen atoms having an atomic number of from 9 to 53, inclusive, $R^2$ is a hydrogen atom or a methyl group, $X^1$ is phenoxy, benzyl or phenylthio, $X^2$ is a halogen atom having an atomic number of from 9 to 35, inclusive, or is methyl and n is 0, 1 or 2.

3. A method according to claim 2 wherein the solvent is a hydroxylic solvent.

4. A method according to claim 3 wherein the solvent is a lower alkanol containing from 1 to 4 carbon atoms.

5. A method according to claim 4 wherein the solvent is a lower alkanol containing from 1 to 2 carbon atoms.

6. A method according to claim 4 wherein the solvent is methanol.

7. A method according to claim 2 wherein the catalyst is ammonia or a nitrogen base.

8. A method according to claim 7 wherein the catalyst is an alkyl, aralkyl or aryl amine in which each alkyl group contains from 1 to 10 carbon atoms and any aralkyl or aryl group contains from 6 to 20 carbon atoms and 1 to 2 hydrocarbyl rings.

9. A method according to claim 8 wherein the amine is a tertiary alkyl amine in which each alkyl group contains from 1 to 4 carbon atoms.

10. A method according to claim 9 wherein the tertiary amine is triethylamine.

11. A method according to claim 2 wherein the solvent is a lower alkanol and the catalyst is an organic amine.

12. A method according to claim 11 wherein the lower alkanol solvent is methanol and the organic amine catalyst is triethylamine.

13. A method according to claim 7 wherein the catalyst is ammonia.

14. A method according to claim 2 wherein the solvent is a lower alkanol and the catalyst is ammonia.

15. A method according to claim 14 wherein the solvent is methanol.

16. A method according to claim 2 wherein the precipitation of crystals of phenylacetate X is conducted with the addition of seed crystals of phenylacetate X.

17. A method according to claim 4 wherein the precipitation of crystals of phenylacetate X is conducted with the addition of from about 0.05 to about 10% of seed crystals of phenylacetate X based upon the phenylacetate in solution.

18. A method according to claim 6 wherein the precipitation of crystals of phenylacetate X is conducted with the addition of greater than 5% of seed crystals of phenylacetate X based upon the phenylacetate in solution.

19. A method according to claims 11 or 14 wherein in the compound of formula I $R^1$ is a halogen atom or an optionally halogenated alkyl or alkoxy group, $R^2$ is a hydrogen atom, $X^1$ is 3-phenoxy and n is 0.

20. A method according to claim 7 wherein in the compound of formula I, $R^1$ is chlorine or difluoromethoxy.

21. A method according to claim 20 wherein $R^1$ is chlorine.

22. A method according to claim 2 wherein an acidic acting material is added to the racemic phenylacetate to prevent epimerization.

23. A method according to claim 22 wherein the acidic acting material is a lower alkanoic acid.

* * * * *